United States Patent
Hopkins et al.

(10) Patent No.: US 8,251,944 B2
(45) Date of Patent: Aug. 28, 2012

(54) SURGICAL SYSTEM HAVING A CASSETTE WITH AN ACOUSTIC COUPLING

(75) Inventors: Mark A. Hopkins, Mission Viejo, CA (US); Nader Nazarifar, Laguna Nigel, CA (US); Jeffrey J. Chun, Irvine, CA (US); David L. Williams, Newport Beach, CA (US)

(73) Assignee: Novartis AG, Basel (CH)

( * ) Notice: Subject to any disclaimer, the term of this patent is extended or adjusted under 35 U.S.C. 154(b) by 1591 days.

(21) Appl. No.: 11/391,748

(22) Filed: Mar. 29, 2006

(65) Prior Publication Data

US 2007/0232990 A1 Oct. 4, 2007

(51) Int. Cl.
*A61M 1/00* (2006.01)

(52) U.S. Cl. ............ 604/30; 604/131; 73/861.25

(58) Field of Classification Search ........... 604/30, 604/131, 246, 118; 417/477.2; 73/861.25, 73/861.26
See application file for complete search history.

(56) References Cited

U.S. PATENT DOCUMENTS

| | | | |
|---|---|---|---|
| 4,395,258 A | 7/1983 | Wang et al. | |
| 4,479,761 A | 10/1984 | Bilstad et al. | |
| 4,493,695 A | 1/1985 | Cook | |
| 4,592,741 A | 6/1986 | Vincent | |
| 4,627,833 A | 12/1986 | Cook | |
| 4,704,909 A | 11/1987 | Grahn et al. | |
| 4,713,051 A | 12/1987 | Steppe et al. | |
| 4,758,238 A | 7/1988 | Sundblom et al. | |
| 4,773,897 A | 9/1988 | Scheller et al. | |
| 4,790,816 A | 12/1988 | Sundblom et al. | |
| 4,798,580 A | 1/1989 | DeMeo et al. | |
| 5,267,956 A | 12/1993 | Beuchat | |
| 5,273,517 A * | 12/1993 | Barone et al. | 494/37 |
| 5,282,787 A | 2/1994 | Wortrich | |
| 5,364,342 A | 11/1994 | Beuchat et al. | |
| 5,463,906 A * | 11/1995 | Spani et al. | 73/861.27 |
| 5,499,969 A | 3/1996 | Beuchat et al. | |
| 5,514,102 A | 5/1996 | Winterer et al. | |
| 5,697,910 A * | 12/1997 | Cole et al. | 604/153 |
| 5,746,241 A | 5/1998 | Stedman | |
| 5,747,824 A | 5/1998 | Jung et al. | |
| 6,039,694 A | 3/2000 | Larson et al. | |
| 6,098,466 A | 8/2000 | Shkarlet | |
| 6,171,280 B1 | 1/2001 | Imazu et al. | |

(Continued)

FOREIGN PATENT DOCUMENTS

CA 2127039 3/1996

(Continued)

OTHER PUBLICATIONS

Shigeyuki, I; Bibliographic data: JP2004257738 (A); abstract only; espacenet.com; 1 page.

(Continued)

*Primary Examiner* — Kevin C Sirmons
*Assistant Examiner* — Laura Schell

(57) ABSTRACT

A surgical cassette have a rigid fluid channel formed into a rigid plastic component or housing. The housing serves as a substrate for an elastomeric acoustic coupling that can be formed on the housing outside of the fluid channel by an over molding process. Such a construction method eliminates the need for adhesives to attach the elastomeric acoustic coupling to the housing and ensures the removal of any air from between the elastomeric acoustic coupling and the housing.

1 Claim, 4 Drawing Sheets

U.S. PATENT DOCUMENTS

| | | |
|---|---|---|
| 6,511,454 B1 | 1/2003 | Nakao et al. |
| 6,517,487 B1 | 2/2003 | Mazess et al. |
| 6,554,822 B1 | 4/2003 | Holschneider et al. |
| 6,599,277 B2 | 7/2003 | Neubert |
| 6,715,366 B2 | 4/2004 | Ohnishi |
| 6,908,451 B2 | 6/2005 | Brody et al. |
| 7,168,930 B2 | 1/2007 | Cull et al. |
| 7,392,144 B2 | 6/2008 | Sorensen et al. |
| 2002/0108450 A1 | 8/2002 | Ohnishi |
| 2003/0101826 A1 | 6/2003 | Neubert |
| 2003/0190244 A1 | 10/2003 | Davis et al. |
| 2003/0195420 A1 | 10/2003 | Mendlein et al. |
| 2004/0039431 A1 | 2/2004 | Machold et al. |
| 2004/0050154 A1 | 3/2004 | Machold et al. |
| 2005/0245888 A1 | 11/2005 | Cull |
| 2007/0005030 A1 | 1/2007 | Hopkins et al. |
| 2007/0073068 A1 | 3/2007 | Quaedflieg et al. |
| 2007/0107490 A1 | 5/2007 | Artsyukhovich et al. |
| 2007/0219494 A1 | 9/2007 | Gao et al. |
| 2007/0244427 A1 | 10/2007 | Nazarifar |
| 2008/0240951 A1 | 10/2008 | Domash et al. |

FOREIGN PATENT DOCUMENTS

| | | |
|---|---|---|
| EP | 1840534 B1 | 9/2009 |
| EP | 1840533 B1 | 9/2010 |
| WO | 9318802 A1 | 9/1993 |
| WO | 03047652 A1 | 6/2003 |
| WO | 2007117781 A2 | 10/2007 |

OTHER PUBLICATIONS

Neubert, W.; Bibliographic data: JP2005515806 (T); abstract only; espacenet.com; 1 page.

Yoshihko H. et al.; Bibliographic data: JP2005192890 (A); abstract only; espacenet.com; 1 page.

\* cited by examiner

SURGICAL SYSTEM HAVING A CASSETTE WITH AN ACOUSTIC COUPLING

BACKGROUND OF THE INVENTION

The present invention relates to an ultrasonic flow sensor and more particularly to a surgical system and cassette having an ultrasonic flow sensor.

Conventional ophthalmic surgical instrument systems use vacuum to aspirate the surgical site and positive pressure to irrigate the site. Typically, a cassette is serially connected between the means used to generate pressure and the surgical instrument. The use of cassettes with surgical instruments to help manage irrigation and aspiration flows at a surgical site is well known. U.S. Pat. Nos. 4,493,695 and 4,627,833 (Cook), U.S. Pat. No. 4,395,258 (Wang, et al.), U.S. Pat. No. 4,713,051 (Steppe, et al.), U.S. Pat. No. 4,798,850 (DeMeo, et al.), U.S. Pat. Nos. 4,758,238, 4,790,816 (Sundblom, et al.), and U.S. Pat. Nos. 5,267,956, 5,364,342 (Beuchat) and U.S. Pat. No. 5,747,824 (Jung, et al.) all disclose ophthalmic surgical cassettes with or without tubes, and they are incorporated in their entirety by this reference. Aspiration fluid flow rate, pump speed, vacuum level, irrigation fluid pressure, and irrigation fluid flow rate are some of the parameters that require precise control during ophthalmic surgery.

Prior art devices have used pressure sensors in the aspiration and irrigation lines and calculate fluid flow rates based on the sensed pressure. In the past, measuring of fluid pressures in surgical cassettes has been very precise and as the resistance in the fluid paths is known, fluid flow rates can be calculated reliably from fluid pressure. Recent improvements in the reliability of ultrasonic flow sensors, however, have now made it possible to non-invasively measure fluid flow accurately.

For example, one ultrasonic flow sensor disclosed in U.S. Pat. No. 6,098,466 (Shkarlet) discloses a flow sensor capable of accurately measuring fluid flow in vessels or tubes having decreased sensitivity to flow distribution non-uniformities and decreased overall size by employing multiple angled reflector surfaces which cause incident ultrasonic waves from one or more ultrasonic transducers to pass through the flow volume multiple times and in multiple directions without changing the planar orientation of the ultrasound waves. The wave paths resulting from the multiple reflections and multi-directional illumination of the flow volume decreases the probe's size and sensitivity to spatial distribution non-uniformities. The multiple angled reflector surfaces also permit the transmitting and receiving ultrasonic transducers to be placed close to one another, thereby reducing the overall probe size and making them particularly useful for incorporation in the relatively small fluid flow cassette used in ophthalmic surgery. In order for an ultrasonic flow sensor to work, the transducer must be acoustically coupled to the tubing in which the fluid is flowing so that any air located between the transducer and the tubing is removed. Prior art flow sensors generally use an acoustic gel, such as a high water content hydrogel material, to accomplish the acoustic coupling. When the acoustic coupling needs to be used in connection with a surgical cassette installed within a surgical console, sterility and cleanliness are of concern, making an acoustic gel less desirable than an acoustic coupling that is formed as part of the cassette or the console and that requires no gel.

Canadian Patent Application No. 2,127,039 A1 describes an elastomer for use as an acoustic coupler for ultrasonic devices. As described in this patent application, the difficulty with independently formed elastomeric acoustic couplers is providing intimate contact between the ultrasound transducer and the elastomer so that no air voids are present at the interface. The solution described in this patent application is an elastomer that is extremely soft and flexible and acoustically transparent. These properties allow the use of relatively thick couplers that may be easily compressed by the transducer, thereby providing greater and firmer contact between the transducer and the elastomer.

When used in connection with a surgical cassette installed within a surgical console, a preformed elastomeric acoustic coupler must be either attached to the cassette or to the ultrasound transducer located in the console. The use of an adhesive is undesirable because of the possibility of air bubbles at the interface of the elastomeric coupler and the surface to which it is adhered, and the fact that the adhesive may interfere with the transmission of the ultrasound waves. In addition, an adhesive adds additional interfaces in the acoustic path. Each additional interface degrades the acoustic signal and the sensing system reliability, repeatability and sensitivity.

Accordingly, a need continues to exist for a simple, reliable and accurate acoustic coupler that can be used on or with a surgical cassette.

BRIEF DESCRIPTION OF THE INVENTION

The present invention improves upon the prior art by providing a surgical cassette having a rigid fluid channel formed into a rigid plastic component or housing. The housing serves as a substrate for an elastomeric acoustic coupling that can be formed on the housing outside of the fluid channel by an over molding process. Such a construction method eliminates the need for adhesives to attach the elastomeric acoustic coupling to the housing and ensures the removal of any air from between the elastomeric acoustic coupling and the housing.

Accordingly, one objective of the present invention is to provide a surgical cassette having an acoustic coupling.

Another objective of the present invention is to provide a surgical cassette having an acoustic coupling that is formed on the cassette without the use of adhesives.

Yet another objective of the present invention is to provide a surgical cassette l s having an acoustic coupling that is over molded onto the cassette.

These and other advantages and objectives of the present invention will become apparent from the detailed description, drawings and claims that follow.

DETAILED DESCRIPTION OF THE PREFERRED EMBODIMENTS

Figure 2:
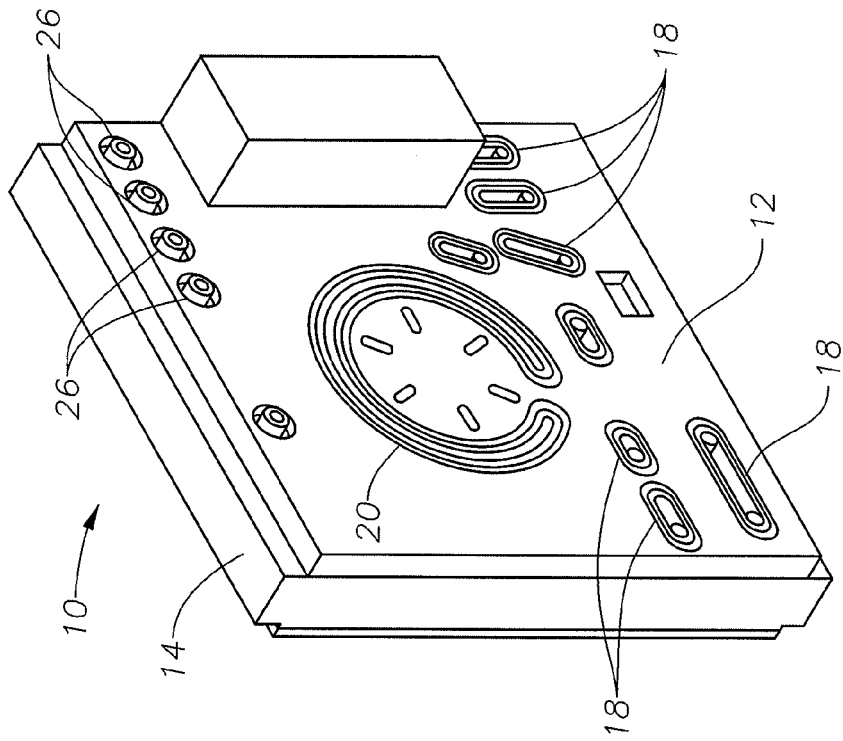
FIG. 2 is a rear perspective view of the cassette of the present invention.
Figure 1:
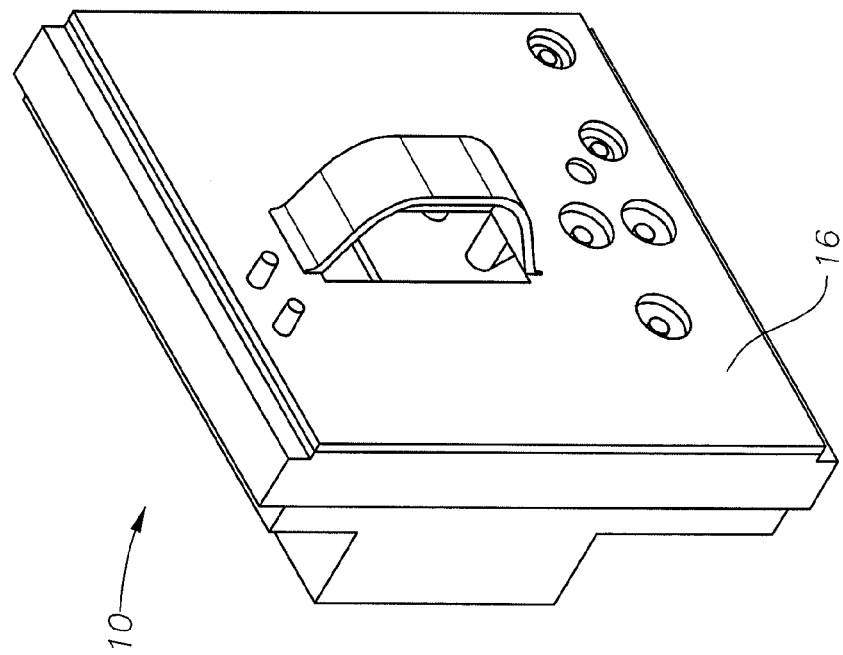
FIG. 1 is a front perspective view of the cassette of the present invention.
Figure 3:
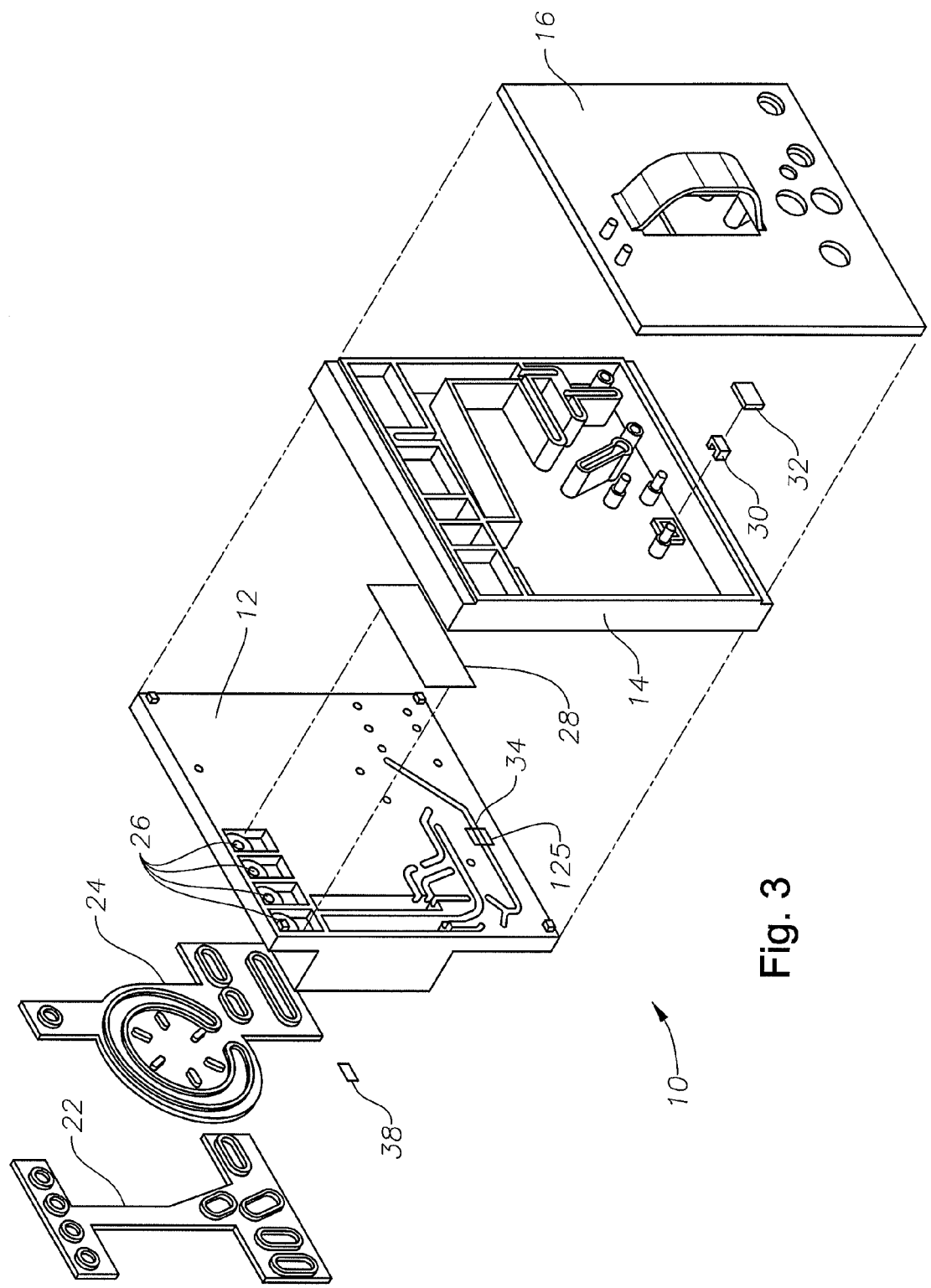
FIG. 3 is an exploded perspective view of the cassette of the present invention.
Figure 4:
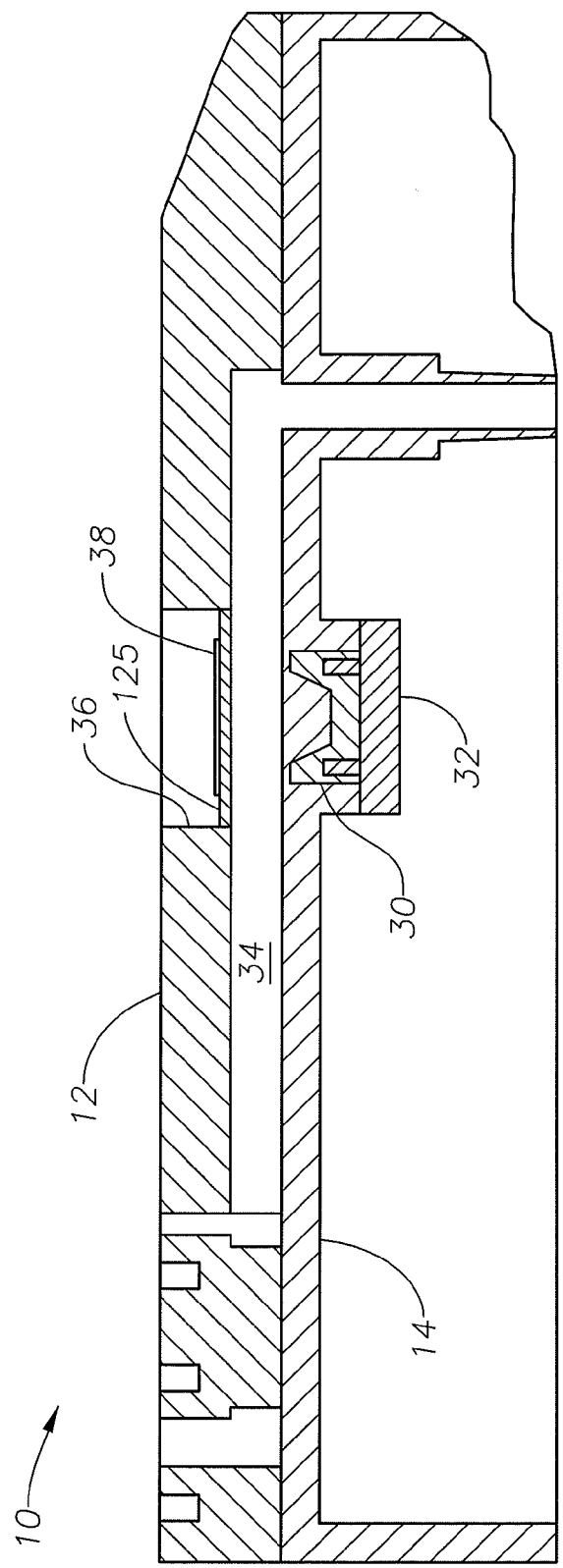
FIG. 4 is a partial cross-sectional view of the cassette of the present invention.
Figure 5:
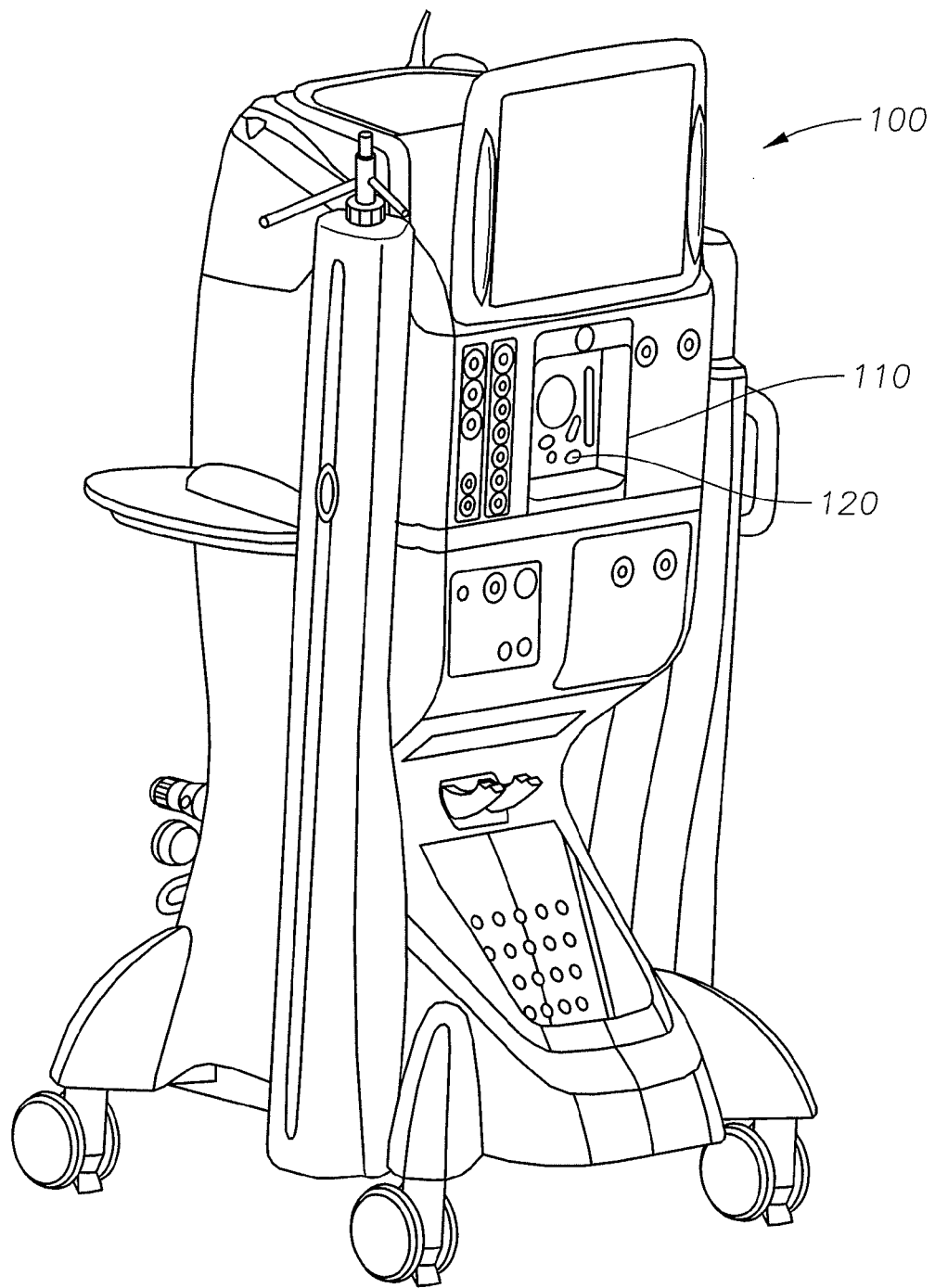
FIG. 5 is a front perspective view of a surgical console that may be used with the cassette of the present invention.

As best seen in FIGS. 1, 2 and 3, cassette 10 of the present invention generally included valve plate 12, body 14 and cover 16. Valve plate 12, body 14 and cover 16 may all be formed of a suitable, relatively rigid, thermoplastic. Valve plate 12 contains a plurality of openings 18 and pumping channel 20 that are sealed fluid tight by elastomers 22 and 24, forming a plurality of fluid paths. Ports 26 provide connectors between cassette 10 and surgical console 100 for the various irrigation and aspiration functions of cassette 10, such functions may requiring the use of filter 28. Attached to body 14 is ultrasound reflector 30 and reflector cover 32. Acoustic reflector 30 and reflector cover 32 may be molded as one piece and are located on body 14 to align with transmission window 125 in recess 36 along fluid passage 34 formed in valve plate 12 when valve plate 12 is assembled onto body 14 in the manner shown in FIG. 3. Located within recess 36 on valve plate 12 is elastomeric acoustic coupler 38. Recess 36 is located adjacent to fluid passage 34 in valve plate 12 and aligned with acoustic reflector 30 and reflector cover 32 when valve plate 12 is assembled on body 14. When cassette 10 is installed in cassette receiving portion 110 of console 100, ultrasound transducer 120 presses against elastomeric acoustic coupler 38, providing an acoustic coupling between transducer 120 and fluid passage 34, thus allowing the use of ultrasound transducer 120 to measure the fluid flow rate in fluid passage 34. Elastomeric acoustic coupler 38 preferably is formed by over molding an elastomeric material, such as a thermoplastic elastomer or silicone rubber within recess 36 of valve plate 12. Such a construction method eliminates the need for adhesives to attach elastomeric acoustic coupler 38 to valve plate 12 and ensures the removal of any air from between elastomeric acoustic coupler 38 and valve plate 12.

This description is given for purposes of illustration and explanation. It will be apparent to those skilled in the relevant art that modifications may be made to the invention as herein described without departing from its scope or spirit.

We claim:
1. A surgical cassette, comprising:
a) a body made from a rigid plastic;
b) a valve plate made from a rigid plastic, coupled to one side of said body, and having:
   a plurality of ports formed therein providing connections between said surgical cassette and a surgical console;
   a recess disposed thereon; and
   a transmission window disposed on a bottom surface of said recess;
c) a plurality of elastomers attached to said valve plate, said elastomers forming a plurality of fluid paths;
d) a cover coupled to an opposite side of said body;
e) an acoustic reflector disposed on said body and aligned with said transmission window;
f) fluid passage defined by said valve plate and said body and aligned with said transmission window; and
g) an elastomeric acoustic coupler attached to said transmission window by over molding.

* * * * *